United States Patent [19]

Hobbs et al.

[11] Patent Number: 5,137,950

[45] Date of Patent: Aug. 11, 1992

[54] 3-9-DIPHOSPHASPIROUNDECANES AND PROCESS FOR MAKING 3-9-DIPHOSPHASPIROUNDECANES

[75] Inventors: Stephen J. Hobbs, Woodstock, Ill.; Kevin J. Sheehan, Parkersburg, W. Va.; William P. Enlow, Belpre, Ohio

[73] Assignee: Borg-Warner Specialty Chemicals, Inc., Parkersburg, W. Va.

[21] Appl. No.: 765,409

[22] Filed: Sep. 25, 1991

Related U.S. Application Data

[63] Continuation of Ser. No. 223,319, Jul. 25, 1988, abandoned.

[51] Int. Cl.$^5$ .............................. C07F 9/15; C08K 5/52
[52] U.S. Cl. .............................. 524/120; 252/400.29; 558/78
[58] Field of Search .................. 252/400.29; 524/120; 558/78

[56] References Cited

U.S. PATENT DOCUMENTS

| | | | |
|---|---|---|---|
| 3,201,437 | 8/1965 | Lester et al. | 558/78 |
| 3,271,481 | 9/1966 | Kujawa et al. | 568/744 |
| 4,066,611 | 1/1978 | Axelrod | 529/114 |
| 4,207,229 | 6/1980 | Spivack | 524/101 |
| 4,290,976 | 9/1981 | Hechenbleikner et al. | 558/78 |
| 4,305,866 | 12/1981 | York et al. | 524/119 |
| 4,312,818 | 1/1982 | Maul et al. | 558/95 |
| 4,371,647 | 2/1983 | Minagawa et al. | 524/120 |
| 4,520,149 | 5/1985 | Golder | 524/100 |
| 4,692,539 | 9/1987 | Spivack | 558/78 |
| 4,692,590 | 9/1987 | Illy et al. | 558/78 |
| 4,739,090 | 4/1988 | Tajima et al. | 558/78 |
| 4,888,371 | 12/1989 | Tajima et al. | 558/78 |

FOREIGN PATENT DOCUMENTS

| | | |
|---|---|---|
| 038876 | 11/1981 | European Pat. Off. . |
| 199997 | 11/1986 | European Pat. Off. . |
| 62-167338 | 7/1987 | Japan . |
| 2156358 | 10/1985 | United Kingdom . |

OTHER PUBLICATIONS

Patent Abstract of Japan, vol. 3, No. 50 of Japanese Reference No. 54-25951 dated Feb. 27, 1979.
Patent Abatracts of Japan, vol. 5, No. 194 dated Dec. 10, 1981 of Japanese Reference no. 56-113790 dated Sep. 7, 1981.

*Primary Examiner*—Kriellion S. Morgan
*Attorney, Agent, or Firm*—Lowe, Price, LeBlanc & Becker

[57] ABSTRACT

The present invention provides an improved process for making diphosphaspiroundecanes and product-by-process, wherein the process comprises reacting a hydroxyl-substituted organic compound, phosphorous trichloride and pentaerythritol to form an organic-substituted diphosphaspiroundecane such that formation of said organic-substituted diphosphaspiroundecane takes place in the presence of a tri-n-alkylamine having n-alkyl moieties such that each n-alkyl moiety has at least three carbon atoms. The present invention is also directed to bis-3,9-(2,6-di-t-alkyl-4-alkylphenoxy)-2,4,8,10-tetroxa-3,9-diphosphaprio[5.5]undecanes and polymer compositions containing an effective amount of same.

40 Claims, No Drawings

3-9-DIPHOSPHASPIROUNDECANES AND PROCESS FOR MAKING 3-9-DIPHOSPHASPIROUNDECANES

This application is a continuation application of application Ser. No. 07/223,319, filed Jul. 25, 1988, now abandoned.

The present invention relates to organic-substituted 3,9-diphosphaspiroundecanes and an improved process whereby organic-substituted 3,9-diphosphaspiroundecanes may be made.

A variety of processes for making organic-substituted 3,9-diphosphaspiroundecanes are known in the art. For example, Japanese Patent Early Disclosure No. 1986-225,191 of Oct. 9, 1986 discloses a process for synthesizing hindered diaryl diphosphaspiroundecanes by reacting phosphorus trichloride, pentaerythritol and an ortho-alkyl phenol in the presence of an amine catalyst such as propyl-, n-butyl, t-butyl, triethyl or tributyl-amine. This catalyst is present in about 0.005-10 wt. % with respect to pentaerythritol. This process is performed in an inert solvent such as xylene.

U.S. Pat. No. 4,094,855 and 4,207,229 to Spivack disclose the synthesis of organic-substituted diphosphaspiroundecanes by reacting 3,9-dichloro-2,4,10-tetroxa-3,9-diphosphaspiroundecane (dichloropentite) with a phenol in the presence of a proton acceptor such as a tertiary amine such as triethylamine.

U.S. Pat. No. 3,271,481 to Kujawa et al. discloses the formation of primary aryl phosphites in tertiary amine such as triethylamine or tributylamine.

U.S. Pat. No. 4,305,866 to York et al. discloses the preparation of substituted diphosphaspiroundecanes by reacting an alkylphenol with a diphenoxy or lower dialkoxy diphosphaspiroundecane and removing the phenol or alkanol formed by distillation.

U.S. Pat. No. 4,371,647 to Minagawa et al. discloses the preparation of substituted diphosphaspiroundecanes by the reaction of a phenol with phosphorus trichloride in chloroform in the presence of triethylamine, followed by reaction with pentaerythritol in the presence of more triethylamine.

A variety of alkylphenoxy diphosphaspiroundecane compounds are known in the art. Japanese Early Disclosure 1986-225,191 of Oct. 9, 1986 by Tajmima et al. mentioned above, discloses a number of bis(alkylphenoxy) diphosphaspiroundecanes, such as, bis(2-tert-butyl-4,6-dimethylphenoxy) diphosphaspiroundecane and bis(2,4-di-t-octylphenoxy) diphosphaspiroundecane. Bis(alkylphenoxy)diphosphaspiroundecanes are also disclosed by U.S. Pat. No. 4,066,611 to Axelrod; U.S. Pat. Nos. 4,094,855 and 4,207,229 to Spivack; U.S. Pat. No. 4,305,866 to York et al.; U.S. Pat. No. 4,520,149 to Golder; U.S. Pat. No. 4,585,818 to Jung et al. and Japanese Patent Application 52 [1977]-110829, Sep. 14, 1977, to Risner et al. Other diphosphaspiroundecane compounds known in the art include bis(2,6-di-t-butyl-4-methylphenoxy) diphosphaspiroundecane and bis(2,6-di-t-butyl-4-ethylphenoxy) diphosphaspiroundecane.

Virtually all commercial polymers contain one or more stabilizing compounds to protect the polymer against degradation of polymer properties by chain scission or undesired crosslinking during processing and product use. This degradation is particularly problematical with thermoplastic polymers, which typically are subjected to extreme processing temperatures. Not only does such degradation effect the physical properties of the composition, but may also cause the polymer to become discolored, thereby making the polymer aesthetically unappealing and cause the product to be rejected.

However, polymer stabilizers may be exposed to various adverse conditions during the course of their production, shipment, storage and use. One such condition which may adversely affect stabilizers is excessive exposure to moisture either in the form of humidity or wetness. Although many stabilizers are used in the form of powders or granules, absorption of moisture may cause a stabilizer to clump or "block" thereby making the stabilizer difficult to handle during feeding and mixing operations. A consequence of such moisture exposure may be hydrolysis, which frequently reduces stabilizing properties and leaves the resin vulnerable to degradation.

Many phosphites, including some of the above-mentioned diphosphaspiroundecanes, may provide excellent stabilization when properly stored, either neat or after being compounded into the polymer. A few phosphites, such as tris(2,4-di-t-butylphenol)phosphite (TBPP), may exhibit good storage stability in humid environments, but do not provide the stabilizing efficacy of many members of the diphosphaspiroundecane class of stabilizer.

Although many of the above diphosphaspiroundecanes are capable of acting as polymer stabilizers, an improvement in the overall balance of properties would be realized if moisture resistance could be improved while maintaining excellent stabilizing properties. Indeed, a stabilizer which imparts good physical and color stability to a polymer while exhibiting improved resistance to moisture and hydrolysis offers significant practical advantages over many stabilizers known in the art.

Known processes for making diphosphaspiroundecanes also suffer from several disadvantages. Many, such as that of Japanese Early Patent Disclosure No. 1986-225,191 and U.S. Pat. No. 4,207,229 and 4,094,855 to Spivack, are performed in a reaction medium such that the product is produced as a solution. Product isolation with such a process requires initial removal of amine-hydrochloride by filtration and subsequent removal of solvent via a distillation process. The product is then purified by crystallization from a second solvent. From a practical standpoint the process is both cumbersome and energy intensive in comparison to a process wherein the product crystallizes directly from the reaction media in which the amine-hydrochloride remains soluble. This would also offer a practical advantage in that the amine could be regenerated without isolation of the hydrochloride salt by simply washing with aqueous base.

It is also preferred that the yield of the desired product be as close as possible to 100% of the theoretical yield since higher yields generally result in more effective use of raw materials and decrease the amount of by-products from which the desired product must be separated and which are available for undesired side-reactions. A process for making diphosphaspiroundecanes which results in high yields of the desired diphosphaspiroundecane product and wherein the desired product is produced as a solid therefore would offer significant practical advantages over many processes known in the art.

SUMMARY OF THE INVENTION

The present invention is a composition which comprises a diphosphaspiroundecane of the general formula:

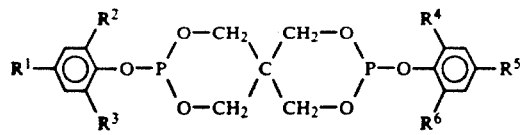

wherein each of $R^2$, $R^3$, $R^4$, and $R^6$ is a tertiary alkyl moiety and each of $R^1$ and $R^5$ is a secondary alkyl moiety. In the embodiment which is preferred $R^2$, $R^3$, $R^4$, and $R^6$ are selected from the group consisting of $C_4$ to about $C_{12}$ tertiary alkyl moieties with tertiary-butyl being the moiety which is most preferred. It is also preferred that $R^1$ and $R^5$ be secondary-butyl moieties.

The present invention includes a stabilized polymer composition which comprises a polymer and an effective amount of the diphosphaspiroundecane of the invention. Thermoplastic polymers are preferred, with polyethylene, polypropylene, polyethylene terephthalate, polyphenylene ether, polystyrene, impact polystyrene and ABS-type graft copolymers being most preferred.

The present invention further comprises a process for making an organic-substituted diphosphaspiroundecane comprising reacting a hydroxyl-substituted organic compound, phosphorous trichloride and pentaerythritol to form said organic-substituted diphosphaspiroundecane such that formation of said organic-substituted diphosphaspiroundecane takes place in the presence of a tri-n-alkylamine having n-alkyl moieties such that each n-alkyl moiety has at least three carbon atoms. It is preferred that the tri-n-alkylamine be present in an amount which is at least the molar equivalent of the acid produced by this reaction.

The present invention is also directed to the product of the embodiment of the process of the invention which employs dichloropentite, and to polymer compositions which include this product.

DETAILED DESCRIPTION OF THE INVENTION

The present invention comprises a 3,9-bis(2,6-di-t-alkyl-4-s-alkyl phenoxy)-2,4,8,10-tetroxa-3,9-diphosphaspiro[5.5]undecane. These compounds, also known as bis(2,6-di-t-alkyl--4-s-alkylphenyl) pentaerythritol diphosphites, may be represented by the general formula:

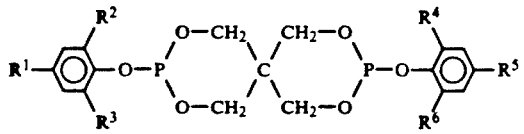

wherein each of $R^2$, $R^3$, $R^4$, and $R^6$ are tertiary (or "tert" or "t") alkyl moieties and wherein each of $R^1$ and $R^5$ are secondary (or "sec" or "s") alkyl moieties.

Examples of tertiary moieties include t-butyl, t-pentyl, 1,1,4,4-tertramethyl butyl, t-octyl, 1-methyl cyclohexyl, t-dodecyl, and 2-phenyl-2-propyl. However, $C_4$ to about $C_{12}$ moieties, such as t-butyl, t-pentyl, t-octyl and t-dodecyl are preferred. Relatively smaller groups, such as t-butyl, t-pentyl, 1-methylcyclohexyl and 1,1,4,4-tetramethyl butyl are more preferred. Tertiary butyl moieties are most preferred. Although any or all of $R^2$, $R^3$, $R^4$ and $R^6$ may be selected to be different, such as in 2-t-butyl-4-s-butyl-6-t-pentylphenoxy, it is preferred that $R^2$, $R^3$, $R^4$ and $R^6$ be the same.

Examples of secondary alkyl moieties include s-butyl, s-pentyl, iso-propyl, s-hexyl, s-decyl, cyclopentyl, cylohexyl and cyclooctyl. However, $C_3$ to about $C_6$ moieties, such as s-butyl, s-pentyl, iso-propyl and cyclohexyl are preferred. Relatively smaller groups, such as s-butyl and s-pentyl are more preferred, with s-butyl being particularly preferred. Although $R^1$ and $R^5$ may be selected to be different, such as when $R^1$ is s-butyl and $R^5$ is s-pentyl, it is preferred that $R^1$ and $R^5$ be selected to be the same.

The diphosphaspiroundecanes of the present invention may be made by means known in the art, such as by the reaction of a di-t-alkyl-s-alkylphenol with 3,9-dichloro-2,4,8,10-tetroxa-3,9-diphosphaspiro[5.5]undecane (which may be formed by the reaction of pentaerythritol with phosphorous trichloride by means known in the art). For example, 3,9-bis(2,6-di-t-butyl-4-s butylphenoxy)-2,4,8,10-tetroxa-3,9-diphosphaspiro[5.5]undecane may be formed by the reaction of 2,6-di-t-butyl-4-s-butylphenol with 3,9-dichloro-2,4,8,10-tetroxa-3,9-diphosphaspiro[5.5]undecane (dichloropentite). Similarly, 3,9-bis(2,6-di-t-pentyl-4-s-butylphenoxy)-2,4,8,10-tetroxa-3,9-diphosphaspiro [5.5] undecane may be formed by the reaction of 2,6-di-t-pentyl-4-s-butylphenol with dichloropentite. Other 3,9-bis(tri-t-alkylphenoxy)-2,4,8,10-tetroxa-3,9-diphosphaspiroundecanes may be formed by reacting the di-t-alkyl-s-alkylphenol corresponding to the desired di-t-alkyl-s-alkyl-s-alkylphenoxy group with dichloropentite.

The diphosphaspiroundecanes of the present invention may also be made by reacting a phenol corresponding to the desired di-t-alkyl-s-alkylphenoxy group with phosphorus trichloride to form a di-t-alkyl-s-alkylphenoxy phosphorodichloridite, followed by reaction of the phosphorodichloridite with pentaerythritol to form a 3,9-bis(di-t-alkyl-s-alkylphenoxy)-2,4,8,10-tetroxa-3,9-diphosphaspiroundecane. For example 2,6-di-t-butyl-4-s-butylphenol may be reacted with phosphorus trichloride and then with pentaerythritol to form 3,9-bis(2,6-di-ti-butyl-4-s-butylphenoxy) -2,4,8,10-tetroxa-3,9-diphosphaspiroundecane. Similarly, 2,6-di-t-dodecyl-4-s-pentylphonol might be reacted with phosphorus trichloride and then with pentaerythritol to form 3,9-bis(2,6-di-t-dodecyl-4-s-pentylphenoxy)-2,4,8,10-tetroxa-3,9-diphosphaspiroundecane.

Procedures for forming diphosphaspiroundecanes by the dichloropentite and the phosphorodichloridite routes are known in the art. However, whereas the prior art may show the diphosphaspiroundecane being formed in solution in the presence of an amine, such as triethylamine, which serves as an acid acceptor by forming an insoluble hydrochloride salt, it is preferred that the diphosphaspiroundecane be formed according to the process of the invention, described below.

The present invention includes an improved process for making organic-substituted diphosphaspiroundecanes including the bis(2,6-di-t-alkyl-4-s-alkylphenoxy) diphosphaspiroundecanes discussed above. This process involves reacting a hydroxyl-substituted organic compound, phosphorus trichloride and pentaerythritol to form an organic-substituted diphosphaspiroundecane, wherein the improvement comprises the formation of the organic-substituted diphosphaspiroundecane taking place in the presence of a tri-n-alkylamine.

It is critical to the invention that the tri-n-alkylamine be one wherein each n-alkyl moiety has at least three carbon atoms, such as n-propyl, n-butyl, n-pentyl and n-hexyl, and preferably less than 10 carbon atoms. N-butyl and n-pentyl moieties are preferred, such as in tri-n-butyl amine, tri-n-pentyl amine and di-n-butyl-n-pentylamine. Tri-n-butylamine is particularly preferred.

The reaction usually will be performed using one of two sequences. In one sequence ("dichloropentite route") phosphorus trichloride is reacted with pentaerythritol to form 3,9-dichloro-2,4,8,10-tetroxa -3,9-diphosphaspiroundecane (also known as "dichloropentite" or "dichloropentaerythritol diphosphite"), followed by reaction of the dichloropentite with the hydroxyl-substituted organic compound in the presence of the tri-n-alkylamine to form the organic substituted diphosphaspiroundecane. In the other sequence ("dichloridite route") phosphorus trichloride and the hydroxyl-substituted organic compound are reacted to form a phosphorodichloridite, followed by reaction of the phosphorodichloridite with pentaerythritol in the presence of the tri-n-alkylamine to form an organic-substituted diphosphaspiroundecane.

The tri-n-alkylamine usually will be present in an amount which is at least sufficient to substantially neutralize the acid formed during the formation of the diphosphaspiroundecane. For example, if the diphosphaspiroundecane is formed by reaction of a hydroxyl-substituted organic compound with dichloropentite, wherein two moles of hydrogen chloride are liberated, the tri-n-alkylamine should be present at least in an amount equal to about two moles of tri-n-alkylamine per mole of dichloropentite. Similarly, if the diphosphaspiroundecane is formed by reaction of pentaerythritol with an organic phosphorodichloridite, the tri-n-alkylamine will be present in an amount at least approximately equal to two moles of tri-n-alkylamine to one mole of phosphorodichloridite. However, it is preferred that a molar excess of tri-n-alkylamine be used.

According to the process of the invention, formation of the diphosphaspiroundecane takes place in a reaction medium which includes the tri-n-alkylamine. The reaction medium may also include solvents such as xylene, chlorobenzene, toluene, ethylbenzene and the like. The relative proportions of co-solvent to tri-n-alkylamine is limited only by the requirement that the amine be present to the molar extent required to neutralize the theoretical quantity of liberated hydrogen chloride and by solubility considerations. Minor amounts of other chemicals, such as catalysts, may also be included. According to the invention, the reaction medium is selected so that the reaction medium is one in which the desired diphosphaspiroundecane product is substantially insoluble, thereby facilitating product separation. It is also preferred that the tri-n-alkylamine and the reaction medium be selected so that the tri-n-alkylamine is one having a hydrogen chloride salt which is substantially soluble in the reaction medium so that significant amounts of the chloride salt do not precipitate under the conditions of the reaction and product separation.

Consistent with the invention, the hydroxyl-substituted organic compound may be any of a variety of hydroxyl-substituted organic compounds, including alkanols, phenols, and hydroxyl-substituted cycloalkanes, and hydroxyl-substituted aralkyls, such as octadecanol, alkylated phenols, cyclohexanol and phenylethanol. However, phenols are preferred, such as 2,4,6-tri-methylphenol, 2,6-di-t-butylphenol, 2,4,6-tri-t-butylphenol, 2,4,-di-t-pentylphenol, and 2,4-di-t-butyl-6-methylphenol. When the dichloropentite route is used, the phenol preferably is selected from the group consisting of 2,4,6-tri-alkyl phenols and 2,4-di-alkyl phenols, such as 2,4,6-tri-t-butyl phenol, 2,4-di-t-butyl phenol, 2,4,6-tri-t-pentylphenol, 2,6-di-t-butyl-4-sec-butylphenol, 2,4-di-t-butylphenol, and 2-t-butyl-4-methylphenol. However, 2,4-di-t-alkyl phenols such as 2,4-di-t-butylphenol and 2,6-di-t-alkyl-4-alkyl phenols, such as 2,4,6-tri-t-butylphenol, 2,6-di-t-butyl-4-methyl phenol, 2,6-di-t-butyl-4-ethyl phenol, 2,4-di-t-butylphenol, and 2,6-di-t-butyl-4-s-butyl phenol are preferred. The 2,4,6-tri-t-alkyl phenols, 2,6-di-t-alkyl-4-n-alkyl phenols, 2,6-di-t-alkyl-4-s-alkyl phenols and 2,4-di-t-alkyl phenols are most preferred.

If the phosphorodichloridite route is followed, the hydroxyl-substituted organic compound also preferably is a phenol, with 2,4,6-tri-alkyl phenols, as described above, being preferred. However, unlike in the process using the dichloropentite route, di-alkyl phenols other than those containing 2,6-dialkyl substitution are not preferred due to the fact that their generally greater reactivity may lead to complications during phosphorodichloridite preparation. Phenols selected from the group consisting of 2,4,6-tri-t-alkyl phenols, 2,6-di-t-alkyl-4-methyl phenols, 2,6-di-t-alkyl-4-ethyl phenols and 2,6-di-t-alkyl-4-s-alkyl phenols, as described above, are more preferred. 2,4,6-tri-t-butyl phenol, 2,6-di-t-butyl-4-methyl phenol, 2,6-di-t-butyl-4-ethyl phenol and 2,6-di-t-butyl-4-s-butyl phenol are particularly preferred.

In the process of the invention employing the dichloropentite route it is preferred that the molar ratio of the hydroxyl-substituted organic compound to the dichloropentite (3,9-dichloro2,4,8,10-tetroxa-3,9-diphosphaspiroundecane) be about 2:1 to about 3:1. In the process using the phosphorodichloridite route it is preferred that the molar ratio of the phosphorodichloridite to pentaerythritol be about 2:1, unless oligomeric products are desired.

The present invention also includes improvement in the preparation of phosphoro-dichloridites, such as those useful in the phosphoro-dichloridite route described above. Whereas previous preparations of this compound may require purification via distillation of the desired product, the present invention provides product without the energy intensive distillation step. This improved process for making phosphoro-dichloridites comprises contacting a hydroxyl-substituted organic compound with phosphorus trichloride in a reaction medium which includes triethylamine. Triethylamine should be present in an amount at least sufficient to substantially neutralize the liberated hydrogen chloride. Although phosphorus trichloride serves as the reaction solvent, the reaction medium may optionally include co-solvents such as toluene or other hydrocarbons.

The improved process for making phosphoro-dichloridites also requires that the molar ratio of phosphorus trichloride to hydroxyl-substituted organic compound be greater than 3:1, with molar ratios of about 3.5:1 or more being preferred. Molar ratios of about 4.5:1 or less are even further preferred.

The improved process provides a simplified isolation and purification sequence. The product is isolated from the reaction medium by first removing amine hydrochloride by filtration, followed by concentration of the filtrate to yield relatively pure phosphoro-dichloridite.

Although a variety of hydroxyl-substituted organic compounds may be used in this improved process for making phosphoro-dichloridites, such as aliphatic alcohols and phenols, this process is particularly useful for hydroxyl-substituted organic compounds such as alkylated phenols.

The present invention also is directed to the product of the dichloropentite route, one of the preferred embodiments of the process of the invention. The preferred product of the process of the invention is that produced by the preferred embodiments of the process of the invention, as described above. In its most preferred embodiment, the product of the invention is that product produced following the dichloropentite route wherein the tri-n-alkylamine is tri-n-butyl amine and is present in an amount sufficient to neutralize substantially all of the hydrochloride produced in the reaction of the dichloropentite with the hydroxyl-substituted organic compound. The preferred product is that produced using a phenol, and more preferably 2,4,6-trialkyl and 2,4-di-alkyl phenols as the hydroxyl-substituted organic compound. Especially preferred are 2,4-di-t-alkyl phenols, such as 2,4-di-t-butyl phenol, and 2,6-di-t-alkyl-4-alkyl phenols, such as 2,4,6-tri-t-butyl phenol, 2,6-di-t-butyl-4-methyl phenol, 2,6-di-t-butyl-4-ethyl phenol, and 2,6-di-t-butyl-4-s-butyl phenol.

The present invention also is directed to stabilized polymer compositions which include at least one of the diphosphaspiroundecane composition of the invention and/or the diphosphaspiroundecane product of the process of the invention, as described above.

An amount of the diphosphaspiroundecane composition of the invention or the product by process of the invention is considered to be an "effective amount", when the polymer composition containing the composition or product of the invention shows improved stability in any of its physical or color properties in comparision to an analogous polymer composition which does not include a composition or product of the invention. In most polymer compositions, however, it will be preferred that the composition or product of the invention be present in an amount equal to about 0.01 to about 2 parts weight per 100 parts by weight resin (phr). Amounts of about 0.01 to about 1 phr are more preferred, although most compositions will contain about 0.025 phr or more.

The polymer may be any of the polymers known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinylchloride/ABS or other impact modified polymers, such as methacrylontrile containing ABS, and polyester/ABS or polyester plus some other impact modifier may also be used. Such polymers are available commercially or may be made by means well known in the art. However the diphosphaspiroundecanes of the invention are particularly useful in thermoplastic polymers, such as polyolefins, polycarbonates, polyesters, polyphenylene ethers and styrenic polymers, due to the extreme temperatures at which the thermoplastic polymers are often processed and/or used.

Polymers of monoolefins and diolefins, for example polypropylene, polyisobutylene, polybutene-1, polymethylppentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example mixtures of polypropylene with (PP) polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene/isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicylopentadiene or ethylidene-norbornene; as well as mixtures of such copolymers and their mixtures with polymers mentioned above, for example polypropylene/ethylene-propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(alpha-methylstyrene), copolymers of styrene or alpha-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate/ styrene/acrylonitrile/methylacrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene. Styrenic polymers may additionally or alternatively include graft copolymers of styrene or alpha-methylstyrene such as, for exa..iple, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs such as methacrylonitrile, such as polyacrylonitrile, acrylonitrile/butadiene polymers, acrylonitrile/alkyl acrylate polymers, acrylonitrile/alkyl methacrylate/butadiene polymers, ABS, and ABS which includes methacrylonitrile.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymer, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride-isoprene copolymer, vinyl chloride-chlorinated propylene copolymer, vinyl chloride-vinylidne chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acid and diols and/or from hydroxycarboxylic acids or the corresponding lactones, such as polyethylene terephthalate, polybutylene terephthalate, poly-1,4-dimethyiol-cyclohexane terephthalate, poly-[2,2-4(4-hydroxyphenyl)-propane] terephthalate and polyhydroxybenzoates as well as block-copolyetheresters derived from polyethers having hydroxyl end groups.

Polyamides and copolyamides which are derived form diamines and dicarboxylic acids and/or from aminocarboxylic acids or the corresponding lactems, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifer, for example poly-2,4,4,-trimethylhexamethylene terephthalamide or poly-m-phenylene isophthalamide may be useful. Further copolymers of the aforementioned polyamides with polyolefins, olefin copolymers, ionomers or chemically boned or grafted elastomers; or with polyethers, such as for instance with polyethylene glycol, polypropylene glycol or polytetramethylene glycols, and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following.

1. Antioxidants 1.1 Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4i-butylphenol, 2,6-di-cyclopentyl-4-methylphenol, 2-(alpha-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol.

1.2 Alkylated hydroquinones for example, 2,6di-tert-butyl-4-methoxyphenol, 2,5-di-tert-butyl-hydroquinone, 2,5-di-tert-amyl-hydroquinone, 2,6-diphenyl-4-octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

1.4 Alkyliden-bisphenols, for example, 2,2'-methylene-bis-(6-tert-butyl-4-methylphenol), 2,2'-methylene-bis-(6-tert-butyl-4-ethylphenol), 2,2'-methylene-bis-[4-methyl-6-(alpha-methylcyclohexyl)phenol], 2,2'-methylene-bis-(4-methyl-6-cyclohexylphenol), 2,2'-methylene-bis-(6-nonyl-4-methylphenol), 2,2'-methylene-bis-[6-(alpha-methylbenzyl)-4-nonylphenol], 2,2'-methylene-bis-[6-(alpha,alpha-dimethylbenzyl)-4-nonylphenol], 2,2'-methylene-bis-(4,6-di-tert-butylphenol), 2,2'-ethylidene-bis-(4,6-di-tert-butylphenol), 4,4'-methylene-bis-(6-tert-butyl-2-methylphenol), 1,1-bis-(5-tert-butyl-4-hydroxy-2-methylphenyl)butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3dodecylmercaptobutane, ethylenglycol-bis-[3,3bis-(3'-tert-butyl-4'-hydroxy-phenyl)-butyrate], di-(3-tert-butyl-4-hydroxy-5-methylphenyl)-dicyclopentadiene, di-[2-(3'-tert-butyl-2'-hydroxy-5'methyl-benzyl)-6-tert-butyl-4-methylphenyl]-terephthalate.

1.5 Benzyl compounds, for example, 1,3,5-tris-(3,5-di-tert-butyl-4-hydroxybenzyl)-2,4,6-trimethylbenzene, bis(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiolterephthalate, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, dioctadecyl 3,5-di-tert-butyl-4-hydroxybenzyl-phosphonate, calcium salt of monoethyl 3,5-di-tert-butyl-4-hydroxybenzylphosphonate, 1,3,5-tris-1,3,5-dicyclohexyl-4-hydroxybenzyl) isocyanurate.

1.6 Acylaminophenols, for example, 4-hydroxy-lauric acid anilide, 4-hydroxy-stearic acid anilide, 2,4-bis-octylmercapto-6-(3,5-tert-butyl-4-hydrox-yanilino)-s-triazine, octyl-N-(3,5-di-tert-butyl-4-hydroxyphenyl)-carbamate.

1.7 Esters of beta-(3,5-di-tert-butyl-4-hydroxyphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentyglycol, tris-hydroxyethyl isocyanurate, thiodiethyleneglycol, di-hydroxyethyl oxalic acid diamide.

1.9 Esters of beta-(5-tert-butyl-4-hydroxy-3-methylphenyl)propionic acid with mono-or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10 Amides of beta-(3,5-di-tert-butyl-4-hydroxyphenyl)-propionic acid for example, N,N'-di-(3,5-di-tert-butyl-4-hydroxyphenylpropionyl)-hexamethylendiamine, N,N'-di(3,5-di-tert-butyl-4-hydroxyphenylpropionyl)-trimethylendiamine, N,N'-di-(3,5-di-tert-butyl-4-hydroxyphenylpropionyl)-hydrazine.

2. UV absorbers and light stabilizers.

2.1 2-(2'-Hydroxyphenyl)-benzotriazoles, for example, the 5'methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3', 5'-di-tert-amyl-, 3',5'-bis-(alpha,alphadimethylbenzyl)-derivatives.

2.2 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3 Ester of substituted and unsubstituted benzoic acids for example, phenyl salicylate, 4-tert-butyl-phenylsalicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

2.4 Acrylates, for example, alpha-cyano-beta,beta-diphenylacrylic acid ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2hydroxy-4-methyl-penyl undecyl ketoxime, nickel complexes of 1-phenyl-4-lauroyl-5-hydroxy-pyrazol, optionally with additional ligands.

2.6 Sterically hindered amines, for example bis-(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis-(1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate; 1-hydroxy-2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethylpiperidin-4-yl)-epsilon-caprolactam.

2.7 Oxalic acid diamides, for example, 4,4'-dioctyloxy-oxanilide, 2,2'-di-octyloxy-5,5=-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o-and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, salicyloylamino-1,2,4-triazole, bis-benzyliden-oxalic acid dihydrazide.

4. Phosphites and phosphonites, for example triphenyl phosphite, diphenylalkyl phosphites, phenyldialkyl phosphites, tris(nonyl-phenyl) phosphite, trilauryl phosphite, trioctadecyl phosphite, distearyl pentaerythritol diphosphite, tris(2,4-di-tert-butylphenyl)phosphite, diisodecyl pentaeythritol diphosphite, bis(2,4-di-tert-butylphenyl)pentaerythritol diphosphite, tristearyl sorbitol triphosphite, and tetrakis (2,4-di-tert-butylphenyl) 4,4'-biphenylene diphosphonite.

5. Peroxide scavengers, for example esters of beta-thiodipropionic acid, for example the lauryl stearyl, myristyl or tridecyl esters, mercaptobenzimidazole or the zinc salt of 2-mercaptobenzimidazole, zinc-dibutyl-dithiocaramate, dioctadecyldisulfide, pentaerythritol-tetrakis(beta-dodecylmercapto)-propionate.

6. Polyamide stabilizers, for example copper salts in combination with iodides and/or phosphorus compounds and salts of divalent manganese.

7. Basic co-stabilizers, for example, malam:ne, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, An stearate, Mg stearate, Na ricinoleate and K palmitate, antimony pyrocatecholate or zinc pyrocatecholate.

8. Nucleating agents, for example, 4-tert-butyl-benzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black, graphite.

10. The present invention may also be used in conjunction with aminoxy propanoate derivatives such as methyl-3-[N,N-dibenzylaminoxy]propanoate; ethyl-3-[N,N-dibenzylaminoxy]propanoate; 1,6-hexamethylene-bis[3-(N,N-dibenzylaminoxy)propanoate]; methyl-[2-(methyl)-3(N,N-dibenzylaminoxy)propanoate]; octadecyl-3-[N,N-dibenzyl-aminoxy]propanoic acid; tetrakis[(N,N-dibenzylaminoxy)ethyl carbonyl oxymethyl]methane; octadecyl-3-[N,N-diethyl aminoxy]-propanoate; 3-[N,N-dibenzylaminoxy]propanoic acid potassium salt; and 1,6-hexamethylene bis[3-(N-allyl-N-dodecyl aminoxy)propanoate].

11. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

Hindered phenolic antioxidants may also be present in the polymer composition. Use of diphosphaspiroundecanes of the present invention may result in enhanced polymer protection by reducing the formation of color resulting from the presence of the phenols. Such phenolic antioxidants include n-octadecyl 3,5-di-tert-butyl-4-hydroxyhydrocinnamate, neopentaneterayl tetrakis-(3,5-di-tert-butyl-4-hydroxyl-hydrocinnamate), di-n-octadecyl 3,5-ti-tert-butyl-4-hydroxybenzyl-phosphonate, 1,3,5-tris(3,5-di-tert-butyl-4-hydroxybenzyl-)isocyanurate, thiodiethylene bis(3,5-di-tert-butyl-4-hydroxyhydrocinnamate). 1,3,5-trimethyl-2,4,6-tris(3,5-di-tert-butyl-4-hydroxybenzyl)benzene, 3,6-di-oxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris-(2,6-dimethyl-4-tert-butyl-3-hydroxybenzyl)isocyanurate. 1,1,3-tris-(2-methyl-4-hydroxy-5-tert-butylphenyl)butane, 1,3,5-tris[2-(3,5-di-tert-butyl-4-hydroxyhydrocinnamoloxy)-ethyl]-isocyanurate, 3,5-di-(3,5-di-tert-butyl-4-hydroxybenzyl)-mesitol, hexa-methylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydro-cinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl- 4-hydroxybenzylmercaptoacetate, bis(3,5-di-tert-butyl-4-hydroxyhydrocinnamoyl)hydrazide, and N,N'-bis-[2-(3,5-tert-butyl-4-hydroxyhydroxocinnamoyloxy)-ethyl]-oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5di-tert-butyl-4-hydroxybenzyl)isocyanurate, 2,6-di-tert-butyl-p-cresol or 2,2'-ethylidene-bis(4,6-di-tert-butylphenol).

Other additives, such as oxazaphospholidines, may additionally or alternatively be present.

Likewise, the instant compounds prevent color formation when hindered amine light stabilizers are present, such hindered amines including bis(1,2,2,6,6-pentamethyl-4-piperidyl)-2-n-butyl-2-(3,5-di-tert-butyl-4-hydroxy-benzyl)malonate; bis(2,2,6,6-tertramehtyl-4-piperidyl) sebacate; dimethylsuccinate polymer with 4-hydroxy-2,2,6,6-tertramehtyl-1-piperidinethanol; and polymer of 2,4-dichloro-6-octylamino-s-triazine with N'-(2,2,6,6-tertramethyl-4-piperidyl)hexamethylene diamine.

Consistent with the invention, the diphosphaspiroundecanes of the invention or the product of the process of the invention may be added to the polymer at any time prior to or during fabrication into articles, and may be combined with the polymer by any of a variety of means known in the art, such as by preblending or by being fed directly into fabrication equipment.

The present invention may further be understood by reference to the Specific Embodiments outlined below, which are provided herein to illustrate various aspects of the invention, either by demonstrating an aspect of the invention, such as polymer stabilization or by hydrolysis resistance, or providing a basis for comparison.

SPECIFIC EMBODIMENTS

Acid number, when measured, was determined by one of the following methods. The Sodium Butoxide Method was used to determine acid number for all examples unless indicated otherwise.

POTASSIUM HYDROXIDE METHOD

Bromothymol (0.1% in 1-butanol) indicator solution is added (4–6 drops) to 100 Ml of 1-butanol in a 250 Ml Erlenmeyer flask. The butanol is neutralized to a blue-green endpoint of pH7 with 0.02N methanolic KOH (1.32 gm KOH (ACS, 85%) in anhydrous reagent grade methanol and diluted to 1 liter and standardized against standard 0.1N HCl). The sample to be tested is weighed to the nearest 0.1 gm and added to the flask. When the sample is a solid the contents of the flask are warmed slightly to 176° F. (80° C. ) before addition of the sample. The appropriate sample weight to be used is determined from the following table:

| Weight to be used | Estimated Acid Number |
| --- | --- |
| 20 gm | less than 0.1 |
| 5 gm | 0.1–2.0 |
| 1 gm | greater than 2.0 |

After addition of the sample the flask is swirled to dissolve the sample, and the contents of the flask are then immediately titrated with 0.02N KOH (described above) to a blue-green endpoint.

SODIUM BUTOXIDE METHOD

Bromothymol blue indicator (0.1%) is prepared as described above. A 2 gm sample of the material to be tested is weighed out in a 250 ml Erlenmeyer flask to the nearest 0.01 gm. Methylene chloride (75 ml) is added to another Erlenmeyer flask, followed by 4–6 drops of the bromothymol indicator solution, and the resulting solution is neutralized with 0.02N sodium butoxide (0.46 gm sodium metal dissolved in anhydrous butanol, diluted to 1 liter and standardized against 0.01N HCl) to a blue-green endpoint of pH-7. The neutralized methylene chloride solution is then added to the flask containing the sample and swirled to dissolve the sample. The resulting solution is immediately titrated with 0.02N sodium butoxide (prepared as indicated above) to a blue-green endpoint.

The acid number for either method is obtained from the following equation:

$$\frac{\text{Acid Number}}{\text{(mg. reagent/gm sample)}} = \frac{(M)(N)(56.1)}{S}$$

where:

M = ml. titrating reagent consumed in the titration
N = normality of the titrating reagent
S = weight (gms) of sample Example 1 illustrates the preparation, by a process known in the art, of 3,9-bis(2,4,6-tri-t-butylphenoxy)-2,4,8,10-tetroxa-3,9-diphosphaspiro[5.5]undecane.

EXAMPLE 1

A suspension of 210.1 gms (800 mmols) of 2,4,6-tri-t-butylphenol, 105.9 gms (400 mmols) of 3,9-dichloro-2,4,8,10-tetroxa-3,9-diphosphaspiro[5.5]undecane and 118 mL (847 mmols) of triethylamine was dissolved in 200 mL of chlorobenzene and refluxed and mechanically stirred under a nitrogen atmosphere for 46 hrs. The resulting dark brown suspension was diluted with 500 mL of chlorobenzene and filtered to remove triethylamine hydrochloride formed during the reaction. On cooling the filtrate, 214 gms of wet crystals were obtained. The crystals were recrystallized from toluene containing a small amount (less than 5 volume %) of triethylamine. The product was isolated by filtration to afford 76.2 g (26% yield) of bis(2,4,6-tri-t-butylphenoxy)-tetroxadiphosphaspiroundecane as crystals, with mp 253.5°-256° C. and acid number 3.0 (KOH-methanol method, described above). Further recrystallization from toluene containing a small amount of triethylalmine afforded 48.8 g (17% yield) of the desired product as a white crystalline solid, mp 250°-255° C., acid number 0.99. Infrared, nmr, and mass spectroscopy confirmed the structure of the product.

Example 2 demonstrates preparation of bis(2,4,6-tri-t-butylphenoxy)-tetroxadiphosphaspiroundecane by an embodiment of the dichloropentite route of the process of the invention.

EXAMPLE 2

To a stirred solution of 120.3 g (458 mmol) of 2,4,6-tri-t-butylphenol in 382 mL of tri-n-butylamine under argon was added 60.7 g (229 mmol) of 3,9-dichloro-2,4,8,10-tetroxa-3,9-diphosphaspiro [5.5]undecane. The suspension was then heated and stirred under argon at an internal temperature of 110° C. for 8 hrs. The resulting suspension was allowed to cool to room temperature and 400 mL of isopropyl alcohol added. Solids were isolated by vacuum filtration and washed on the funnel with an additional 1L of isopropyl alcohol and then 1L of n-heptane to afford 145.4 g (89% of theoretical yield) of the desired diphosphaspiroundecane as a white powder, with mp 253°-254° C. and acid number 0.92. This product was confirmed by standard methods. Thus it appears that the above process consistent with that of the present invention gives improved product yield in comparison to the prior art process of Example 1.

Example 3 demonstrates preparation of bis(2,4,6-tri-t-butylphenoxy)-tetroxadiphosphaspiroundecane by an embodiment of the dichloridite route, another embodiment of the process of the invention.

EXAMPLE 3

To 73.0 g (530 mmol) of phosphorus trichloride in an ice water bath was slowly added 16.9 g (170 mmol) of triethylamine. The mixture was stirred for ten minutes and then 35.0 g (130 mmol) of 2,4,6-tri-t-butylphenol was added in 7.0 g portions over a period of 20 minutes with continued cooling. After addition of 2,4,6-tri-t-butylphenol was complete the reaction mixture was heated at reflux for 3.5 hrs. and then allowed to cool to room temperature. The reaction mixture was diluted with 200 mL of heptane and cooled and filtered. The filter cake was washed twice with 80 mL (2 ×80) of heptane. Combined organic filtrates were concentrated under vacuum to afford 48.2 g (99% of theoretical yield) of the dichloridite as a solid product, with mp 81°-86° C. Similar results were obtained when this reaction was carried out in toluene solvent.

In the next step, a mixture of 47.0 g (130 mmol) of 2,4,6-tri-t-butylphenylphosphorodichloridite and 80 mL of toluene was added to 48.8 g (260 mmol) of tributylamine and 8.8 g (65 mmol) of pentaerythritol. An exotherm to 55° C. was accompanied by the formation of a white precipitate. After stirring for one hour the reaction mixture, which had returned to room temperature, was filtered under vacuum and the filter cake washed four times with 50 mL (4×50) of isopropyl alcohol. The resulting filter cake was dried to afford 33.2 g (71% of theoretical yield) of the desired diphosphaspiroundecane as a white solid, mp 253°-257° C., acid number 0.31. This product was confirmed by standard methods. Thus it appears that the process of Example 3, consistent with the process of the present invention, gives improved product yield in comparison to the prior art process of Example 1.

EXAMPLES 4-13

Other spirocyclic compounds (Examples 4-8) were synthesized by substituting the same molar proportion of other phenols for 2,4,6-tri-t-butylphenol in Example 1. Other spirocyclic compounds (Examples 9-12) were also synthesized by substituting the same molar proportion of other phenols for 2,4,6-tri-t-butylphenol in Example 2. These phenols were:

| Example | Phenol |
| --- | --- |
| 4 | 2,6-Di-t-butylphenol |
| 5,9 | 2,6-Di-t-butyl-4-methylphenol |
| 6,10 | 2,6-Di-t-butyl-4-ethylphenol |
| 7,11 | 2,6-Di-t-butyl-4-s-butylphenol |
| 8,12 | 2,4-Di-t-butylphenol |

Synthesis of the analogous diphosphaspiroundecanes, shown in Table I, was confirmed by one or more standard method, such as melting point, infrared spectroscopy (IR), nuclear magnetic resonance spectroscopy (NMR) and mass spectroscopy. The compounds thus prepared were used in the testing discussed in the following examples.

For convenience, the diphosphaspiroundecane products of Examples 1, 4-12 were denoted as indicated below. (All are 3,9-bis(di or tri-alkylphenoxy)-2,4,8,10-tetroxa-3,9-diphosphaspiro[5.5]undecanes. However, all numbering except that of the alkyl substituents on the phenoxy moiety have been deleted below as a matter of convenience.)

Moisture Sensitivity of Substituted 3,9-Bis(2,6-di-t-butyl-4-alkyphenoxy)-2,4,8,10-tetroxa-3,9-diphosphaspiro[5.5]undecanes The moisture sensitivity of the spirocyclic diphosphites of Table I and of TBPP (tris(2,4-di-t-butylphenyl) phosphite, a noncyclic phosphite stabilizer known in the art) were examined by placing the compounds into an atmospheric chamber regulated at about 80% relative humidity at ambient laboratory temperature (about 70° F.). The samples were maintained in the chamber and monitored for weight gain and increase in acid value (AV) with respect to time. (Weight gain is an indication of the hygroscopic nature of the compound and may reflect sample hydrolysis, while an increase in acid value is indicative of some hydrolysis occuring in the sample.) The time required for the compounds to gain 1% weight during moisture exposure was assigned as the failure point. The results are indicated below in Table II. Acid value was measured by the Na-butoxide/methylene chloride method both before the sample was placed in the atmospheric chamber (denoted "Initial AV") and after the sample had attained a 1% weight gain (denoted "Final AV"). Data in Table II indicate that diphosphaspiroundecane compositions prepared by a process consistent with the process of the present invention may exhibit improved moisture properties in comparison to compositions prepared by a process known in the art.

EXAMPLE 14

The procedure of Example 2 was repeated eleven times using slight variations in the relative amount of 2,4,6-tri-t-butylphenol (2.0 to 2.2 relative to chloropentite on a molar basis) and/or tri-n-butylamine present, (3.0 to 6.0 relative to chloropentite on a molar basis). The products of these reactions were then aged in a humid environment under the conditions described above for 2000 hours to demonstrate the consistency of the process with respect to product moisture sensitivity. For the eleven samples tested, the average initial AV was 1.6 (high 5.08, low 0.37). These samples gained an average of 0.7% in weight (low 0.2%, high 1.13%) during the aging period. The average Final AV for these samples was 5 (low 1.6, high 12.4). An additional preparation of Compound E, made from 2,6-di-t-butyl-4-sec-butylphenol, was also aged in this study. The sample had an Initial AV of 0.34, had gained 1.7% weight during the 2000 hours and had attained a Final AV of 18.3.

EXAMPLES 15-21

Compound A and Compound E were prepared according to the procedure of Examples 1 and 7, respectively. Testing of Compound E, consistent with one embodiment of the diphosphaspiroundecane of the invention, and TBPP and Compound A, not embodying the invention, were tested in an LLDPE containing 300 ppm of octadecyl 3,5-di-t-butyl-4-hydroxyhydrocinnamate, and 500 ppm of calcium stearate. Results of this testing are indicated below in Table III.

In these and subsequent examples, powdered calcium stearate and diphosphaspiroundecane (and other additives which were present) were incorporated into the resin by dry blending for 45 minutes in a Turbula blender. The dry blended resin mixture was extruded at a stock temperature of 525° C. through a one-inch single screw extruder equipped with a 2-stage screw fitted with a Maddox mixer. The extrudate was pelletized and reextruded for a total of seven extrusions. Material was saved from the first, third, fifth and seventh extrusions. The melt flow of these samples was measured using ASTM test method D-1238, Condition E.

The melt flow of LLDPE generally decreases with each extrusion as the polymer undergoes degradation by an overall crosslinking reaction, thereby decreasing melt flow. The efficiency of a stabilizer may therefore be evaluated by measuring its melt flow over successive extrusions and determining how close the melt flow of successive extrusions are to the melt flow of the initial extrusion.

The color of the retained samples was measured using a Hunter colormeter and standard techniques prescribed for use with that equipment, and comparing the yellowness index (YI) change between the first and seventh samples of each extrusion. The color measurements were made on one-eighth inch by one and one-half inch diameter discs that were compression molded at 330° F. from the retained sample pellets. Higher values indicate more color-development.

Results of melt flow and color testing of resin containing these compounds are indicated below in Table III. Loading levels of the diphosphaspiroundecanes in the resin are indicated in parts per hundred parts resin. The headings "first, third, fifth, seventh" indicate the number of extrusions the composition had undergone when the sample was taken.

EXAMPLES 22-28

Additional testing of TBPP and Compound A and Compound E, prepared according to Examples 1 and 7, was performed using Profax 6501 poly (propylene) resin from Hercules. The compositions tested included 0.025 phr of pentaerythritol tetrakis [3-(3,5-di-t-butyl-4-hydroxy phenyl)propionate] and 0.05 phr. Ca Stearate. The amount of additive compound present and the results are indicated below in Table IV.

The above examples are presented to illustrate various aspects of the invention. The invention is defined only by the following claims, and is not limited in scope to the particular embodiments or parameters described as modifications of these teachings will be apparent to those skilled in the art in view of the present disclosure.

TABLE I

| Compound | Example | Name |
|---|---|---|
| A | 1,2 | bis(2,4,6-tri-t-butylphenoxy)-tetroxa-diphosphaspiroundecane |
| B | 4 | bis(2,6-di-t-butylphenoxy)-tetroxa-diphosphaspiroundecane |
| C | 5,9 | bis(2,6-di-t-butyl-4-methylphenoxy)-tetroxa-diphosphaspiroundecane |
| D | 6,10 | bis(2,6-di-t-butyl-4-ethylphenoxy)-tetroxa-diphosphaspiroundecane |
| E | 7,11 | bis(2,6-di-t-butyl-4-s-butylphenoxy)-tetroxa-diphosphaspiroundecane |
| F | 8,12 | bis(2,4-di-t-butylphenoxy)-tetroxa-diphosphaspiroundecane |

TABLE II

| Example | Compound | Time to 1% Weight Gain | Initial Av | Final AV |
|---|---|---|---|---|
| 1 | A | 1674 | 0.23 | 4.70 |
| 2 | A | >2200 | 1 | — |
| 4 | B | 96 | 0.54 | 3.32 |
| 5 | C | 66 | 0.26 | 21.60 |
| 9 | C | 1500 | 1.25 | 16 |
| 6 | D | 72 | 2.55 | 9.5 |
| 10 | D | 407 | 0.22 | 8.5 |
| 7 | E | 216 | 0.13 | 7 |
| 11 | E | 947 | 0.85 | 14.2 |
| 8 | F | 66 | 1.06 | 14.2 |
| 12 | F | 336 | 0.53 | 4.3 |
| 13 | TBPP | >1200 | 0.21 | 0.96 |

TABLE III

| Example | Compound | Amount phr | Melt Flow, g/10 min | | | Color, YI | |
|---|---|---|---|---|---|---|---|
| | | | first | third | fifth | first | fifth |
| 15 | — | — | 1.59 | 0.98 | 0.75 | 15.13 | 19.55 |
| 16 | A | 0.04 | 2.04 | 1.27 | 0.93 | 12.63 | 14.90 |
| 17 | A | 0.07 | 1.98 | 1.87 | 1.62 | 11.09 | 13.39 |
| 18 | E | 0.04 | 1.98 | 1.53 | 0.93 | 12.59 | 15.63 |
| 19 | E | 0.07 | 1.94 | 1.88 | 1.71 | 11.28 | 12.66 |
| 20 | TBPP | 0.04 | 1.64 | 1.19 | 0.86 | 13.44 | 18.57 |
| 21 | TBPP | 0.07 | 1.62 | 1.12 | 0.86 | 12.93 | 17.96 |

TABLE IV

| Example | Compound | Amount phr | Melt Flow, g/10 min first | Melt Flow, g/10 min third | Melt Flow, g/10 min fifth | Color, YI first | Color, YI fifth |
|---|---|---|---|---|---|---|---|
| 22 | — | — | 5.7 | 12.4 | 19.4 | 8.9 | 9.78 |
| 23* | A | 0.05 | 2.1 | 2.6 | 3.2 | 9.39 | 9.56 |
| 24* | A | 0.0375 | 2.4 | 2.7 | 3.4 | 9.75 | 9.63 |
| 25 | E | 0.05 | 2.6 | 2.8 | 2.9 | 8.98 | 9.26 |
| 26 | E | 0.0375 | 2.0 | 3.0 | 4.2 | 8.04 | 9.47 |
| 27 | TBPP | 0.05 | 3.3 | 5.2 | 8.3 | 9.08 | 9.24 |
| 28 | TBPP | 0.0375 | 2.9 | 4.8 | 7.3 | 9.56 | 9.57 |

*represents an average of the following values obtained from four different runs:

TABLE V

| Example | Compound | Amount phr | Melt Flow, g/10 min first | Melt Flow, g/10 min third | Melt Flow, g/10 min fifth | Color, YI first | Color, YI fifth |
|---|---|---|---|---|---|---|---|
| 23 | A | 0.05 | 2.0 | 2.7 | 3.4 | 9.06 | 9.16 |
|  |  |  | 2.6 | 2.8 | 3.4 | 9.37 | 9.50 |
|  |  |  | 2.1 | 2.6 | 3.2 | 9.39 | 9.56 |
|  |  |  | 2.1 | 2.3 | 2.7 | 9.25 | 9.56 |
| 24 | A | 0.0375 | 2.1 | 2.4 | 3.4 | 9.78 | 10.38 |
|  |  |  | 2.4 | 2.7 | 3.4 | 9.75 | 9.63 |
|  |  |  | 2.6 | 2.8 | 3.0 | 9.94 | 9.58 |
|  |  |  | 2.8 | 2.9 | 3.2 | 9.37 | 9.83 |

We claim:

1. A process for making an organic-substituted diphosphaspiroundecane comprising first reacting phosphorus trichloride with one of (a) pentaerythritol and (b) a second hydroxyl-substituted organic compound selected from the group consisting of alkanols, phenols, hydroxyl-substituted cycloalkanes and hydroxyl-substituted aralkyls, and second reacting the resulting reaction product with the other of (a) and (b), said second reaction being conducted in the presence of a tri-n-alkylamine in which each n-alkyl moiety has at least three carbon atoms, wherein said tri-n-alkylamine is present in a molar amount which is equal to or greater than the molar amount of hydrogen chloride produced by said second reaction, and wherein said organic-substituted diphosphaspiroundecane is a solid product and substantially insoluble in the medium of the second reaction.

2. The process of claim 1 wherein said tri-n-alkylamine is one having a hydrochloride salt which is substantially soluble in said reaction medium.

3. The process of claim 2 wherein said phosphorous trichloride and said pentaerythritol are reacted to form 3,9-dichloro-2,4,8,10-tetroxa-3,9-diphosphaspiroundecane before reaction with said hydroxyl-substituted organic compound to form said organic-substituted diphosphaspiroundecane.

4. The process of claim 2 wherein said phosphorous trichloride and said hydroxyl-substituted organic compound are reacted to form a phosphorodichloridite before reaction with pentaerythritol to form said organic-substituted diphosphaspiroundecane.

5. The process of claim 2 wherein the n-alkyl moieties of said tri-n-alkylamine have about 3 to about 10 carbon atoms.

6. The process of claim 5 wherein said amine is selected from the group consisting of tri-n-propylamine, tri-n-butylamine and tri-n-pentylamine.

7. The process of claim 6 wherein said tri-n-alkylamine is tri-n-butylamine.

8. The process of claim 1 wherein said reaction medium consists essentially of said tri-n-alkylamine.

9. The process of claim 3 wherein said organic compound is an aliphatic alcohol.

10. The process of claim 3 wherein said organic compound is a phenol.

11. The process of claim 3 wherein said phenol is selected from the group consisting of 2,4,6-tri-alkyl and 2,4-di-alkyl substituted phenols.

12. The process of claim 11 wherein said phenol is selected from the group consisting of 2,4-di-t-alkyl phenols and 2,6-di-t-alkyl-4-alkyl phenols.

13. The process of claim 12 wherein said phenol is selected from the group consisting of 2,4,6-tri-t-alkyl phenols, 2,6-di-t-alkyl-4-n-alkyl phenols, 2,6-di-t-alkyl-4-s-alkyl phenols, and 2,4-di-t-alkyl phenols.

14. The process of claim 13 wherein said phenol is selected from the group consisting of 2,4,6-tri-t-butyl phenol, 2,6-di-t-butyl-4-methyl phenol, 2,6-di-t-butyl-4-ethyl phenol, 2,6-di-t-butyl-4-s-butyl phenol, and 2,4-di-t-butyl phenol.

15. The process of claim 13 wherein said phenol is a 2,6-di-t-alkyl-4-s-alkyl phenol.

16. The process of claim 13 wherein said phenol is a 2,4,6-tri-t-alkyl phenol.

17. The process of claim 3 wherein the molar ratio of said organic compound to said 3,9-dichoro-2,4,8,10-tetroxa-3,9-diphosphaspiroundecane is about 2:1 to about 3:1.

18. The process of claim 4 wherein said organic compound is a phenol.

19. The process of claim 18 wherein said phenol is selected from the group consisting of 2,4,6-tri-alkyl substituted phenols.

20. The process of claim 19 wherein said phenol is selected from the group consisting of 2,4,6-tri-t-alkyl phenols, 2,6-di-t-alkyl-4-methyl phenols, 2,6-di-t-ethyl phenols, and 2,6-di-t-alkyl-4-ethyl phenols, and 2,6-di-alkyl-4-s-alkyl phenols.

21. The process of claim 20 wherein said phenol is selected from the group consisting of 2,4,6-tri-t-butyl phenol, 2,6-di-t-butyl-4-methyl phenol, 2,6-di-t-butyl-4-ethyl phenol, and 2,6-di-t-butyl-4-s-butyl phenol.

22. The process of claim 4 wherein the improvement further comprises the ratio of mole equivalents of phosphorus trichloride to said hydroxyl-substituted organic compound being greater than 3:1.

23. The process of claim 22 wherein the ratio of mole equivalents of phosphorus trichloride to mole equivalents of said organic compound is about 3.5:1 to about 4.5:1.

24. The process of claim 4 wherein said tri-n-alkylamine is present in an amount greater than the stoichiometric amount required to neutralize hydrogen chloride liberated during reaction of said phosphorodichloridite with pentaerythritol.

25. The product of the process of claim 3.

26. The product of claim 25 wherein the n-alkyl moieties of said tri-n-alkylamine have about 3 to about 10 carbon atoms.

27. The product of claim 26 wherein said n-alkyl moieties are n-butyl moieties.

28. The product of claim 24 wherein said reaction medium consists essentially of a tri-n-alkylamine.

29. The product of claim 25 wherein said organic compound is an aliphatic alcohol.

30. The product of claim 25 wherein said organic compound is a phenol.

31. The product of claim 25 wherein said phenol is selected from the group consisting of 2,4,6-tri-alkyl and 2,4-di-alkyl substituted phenols.

32. The product of claim 31 wherein said phenol is selected from the group consisting of 2,4-di-t-alkyl phenols and 2,6-di-t-alkyl-4-alkyl phenols.

33. The product of claim 32 wherein said phenol is selected from the group consisting of 2,4,6-tri-t-alkyl phenols, 2,6-di-t-alkyl-4-methyl phenols, 2,6-di-t-alkyl-4-ethyl phenols, 2,6-di-t-alkyl-4-s-alkyl phenols, and 2,4-di-t-alkyl phenols.

34. The product of claim 33 wherein said phenol is selected from the group consisting of 2,4,6-tri-t-butyl phenol, 2,6-di-t-butyl-4-methyl phenol, 2,6-di-t-butyl-4-ethyl phenol, 2,6-di-t-butyl-4-s-butyl phenol, and 2,4-di-t-butyl phenol.

35. The product of claim 34 wherein said phenol is selected from the group consisting of 2,6-di-t-butyl-4-s-butyl phenol, 2,6-di-t-butyl-4-methylphenol and 2,4-di-t-butylphenol.

36. A polymer composition comprising a polymer and a sufficient amount of the product of claim 25 to improve the melt flow stability and/or the color stability of the polymer.

37. The polymer composition of claim 36 wherein the polymer is selected from the group consisting of polyolefin, polyester, polycarbonate, polyphenylene ether, and styrenic resins, and mixtures thereof.

38. The composition of claim 37 wherein the polymer is selected from the group consisting of polyamide 6, polyamide 6/6, 6/10, 6/9, 6/12 and 4/6, polyethylene, polypropylene, polyethylene terephthalate, polybutylene terephthalate, polyphenylene ether, polycarbonate, polystyrene, impact polystyrene, and ABS-type graft copolymer resins, and mixtures thereof.

39. The polymer composition of claim 36 wherein the product of claim 25 is present in an amount equal to about 0.01 to about 2 phr.

40. The polymer composition of claim 39 wherein the product of claim 25 is present in an amount equal to about 0.01 to about 1 phr.

* * * * *